(12) United States Patent
Nilsson et al.

(10) Patent No.: US 6,622,723 B1
(45) Date of Patent: Sep. 23, 2003

(54) INHALER DOSING DEVICE

(75) Inventors: Thomas Nilsson, Mariefred (SE); Lars-Gunnar Nilsson, Koping (SE)

(73) Assignee: Microdrug AG, Hergiswil (SE)

( * ) Notice: Subject to any disclaimer, the term of this patent is extended or adjusted under 35 U.S.C. 154(b) by 232 days.

(21) Appl. No.: 09/703,796

(22) Filed: Nov. 2, 2000

(30) Foreign Application Priority Data

Nov. 11, 1999 (SE) ................................. 9904081

(51) Int. Cl.$^7$ ................................. A61M 15/00
(52) U.S. Cl. ................................. 128/203.15; 128/203.12
(58) Field of Search ................. 128/200.11, 200.12, 128/200.14, 200.16–200.18, 200.21–200.24, 203.12, 203.15, 203.21, 203.19; 604/58

(56) References Cited

U.S. PATENT DOCUMENTS

| | | | |
|---|---|---|---|
| 5,042,472 A | * 8/1991 | Bunin | 128/203.15 |
| 5,415,162 A | 5/1995 | Casper et al. | |
| 5,642,727 A | * 7/1997 | Datta et al. | 128/203.15 |
| 5,669,973 A | * 9/1997 | Pletcher | 604/58 |
| 6,006,747 A | * 12/1999 | Eisele et al. | 128/203.15 |
| 6,065,472 A | * 5/2000 | Anderson et al. | 128/203.21 |
| 6,230,707 B1 | * 5/2001 | Horlin | 128/203.15 |
| 6,401,712 B1 | * 6/2002 | von Schuckmann | 128/203.15 |
| 6,520,179 B1 | * 2/2003 | Von Schuckmann | 128/203.15 |

FOREIGN PATENT DOCUMENTS

| | | | | |
|---|---|---|---|---|
| GB | WO 93/09831 | * 5/1993 | | |
| WO | WO9700704 | 1/1997 | | |
| WO | WO 97/40876 | * 11/1997 | ............ | 128/203.15 |
| WO | WO9927987 | 6/1999 | | |

* cited by examiner

Primary Examiner—Weilun Lo
Assistant Examiner—Teena Mitchell
(74) Attorney, Agent, or Firm—Young & Thompson

(57) ABSTRACT

A dosing device of an inhaler for administration of a pharmaceutical composition during a prolonged time period is disclosed. The principle of the inspiratory administration is basically utilizing known techniques for administering of the pharmaceutical composition, whereby the fine powder to be administered is gathered as extended doses (15, 16) of powder onto a surface of a dosing member. The disposable dosing member (10) contains a number of prefabricated dose strings to be accessed. A dosing element (7) having an adapted opening moves along an extended string of the dosing member during the administration to in this manner prolong the time period, during which the pharmaceutical composition is released from the dosing member (10) into an air-stream of the inhaler during the inspiration. The relative motion of the dosing element (7) is either obtained by rotating the dosing member itself or moving the dosing element along the surface of the dosing member. Thereby an evenly distributed amount of powder in the inspiration air is obtained during, for instance, one to two seconds of inspiration in accordance with the motion of the dosing element (7) relative to the extended dose of pharmaceutical composition.

17 Claims, 3 Drawing Sheets

INHALER DOSING DEVICE

TECHNICAL FIELD

The present invention relates to dosing device for an inhaler and more particularly to an inhaler dosing device, during an inspiration for administering a pharmaceutical substance, providing a slower administration of the pharmaceutical substance to reach the deep areas of the lung of a patient.

BACKGROUND

Inhalers have been developed from being very simple to the up-to-date relatively complicated devices. For the up-to-date inhalers some form of mechanical dosing is almost entirely used for preparing the dose to be inhaled. Most often the dosing of the amount to be inhaled takes place industrially in advance in the form of a blister pack containing 10–50 doses. The inhaler then is loaded with this blister pack as the source of each dose. Other inhalers have a magazine from which the powder is dosed by some device for distribution to the inspiration air. In both cases the powder will generally be strongly agglomerated and therefore must be dispersed.

This dispersion of the agglomerates today mainly takes place by means of techniques in which the energy of the inspiration air is utilized. A normal inhalation takes place during about two seconds and a peaceful inspiration takes 3–4 seconds. In such designs, in which only the inhalation air is utilized for the de-agglomeration, only a fraction of the energy of the inhalation air will be utilized, as the dose of powder is given normally during only 0.1 to 0.4 s. Consequently this results in a low exploitation of the available energy which as a matter of fact will be present in the inhalation air. As only a small portion of the amount of energy is used it will be too low for a sufficient dispersion to take place. The total respirable dose therefore becomes very dependent on the occasion and the individual patient and thereby very varying from time to time. To improve this condition a number of inhalers include some kind of device against which the powder should collide and thereby transfer energy for de-agglomerating the powder.

However, such a collision with a fixed or mechanically moving object involves that a relatively large amount of powder sticks either permanently or is transported further together with the next dose. In both cases this constitutes a negative factor for the goal of obtaining a high accuracy and quality of the inhaled dose, e.g. an accurate amount of powder having a high portion of very small particles.

In a document WO97/00704 is described an inhaler device in which the substance to be administered is charged electrostatically and the dosing is performed by means of the assistance of a rotating dosing drum attracting the charged particles of the substance. The substance is then emitted from the dosing drum by means of a combination of an additional electric field and the air stream resulting from an inspiration. In advance of a desired dosing step the substance to be administered is kept in a reservoir, loaded for instance by means of receiving a cartridge containing the substance intended for many operations of the device.

There is still a demand for an inhaler device for inhaling a suitable medical substance, by means of which device the inhaled substance will be more even distributed during the entire inspiration than what is presented by inhalers according to the state of the art.

SUMMARY

A dosing device of an inhaler for administering a pharmaceutical composition during a prolonged time period is disclosed. The powder to be administered is gathered as an extended dose or string of fine powder onto an envelope surface of a dosing member. The dosing member contains a number of prefabricated doses to be accessed. A dosing element having an adapted opening moves along the extended dose arrangement of the dosing member during the administration to in this manner prolong the time period, during which the pharmaceutical composition is released from the dosing member into an air-stream of the inhaler during an inspiration. This motion is either obtained by rotating the dosing member itself or moving the dosing element long the surface of the dosing member. Thereby an even distributed amount of very fine powder in the inspiration air is obtained during for instance one to two seconds of inspiration in accordance with the motion of the dosing element or the dosing member.

BRIEF DESCRIPTION OF THE DRAWINGS

The invention, together with further objects and advantages thereof, may best be understood by making reference to the following description taken together with the accompanying drawings, in which.

DETAILED DESCRIPTION

Figure 1:
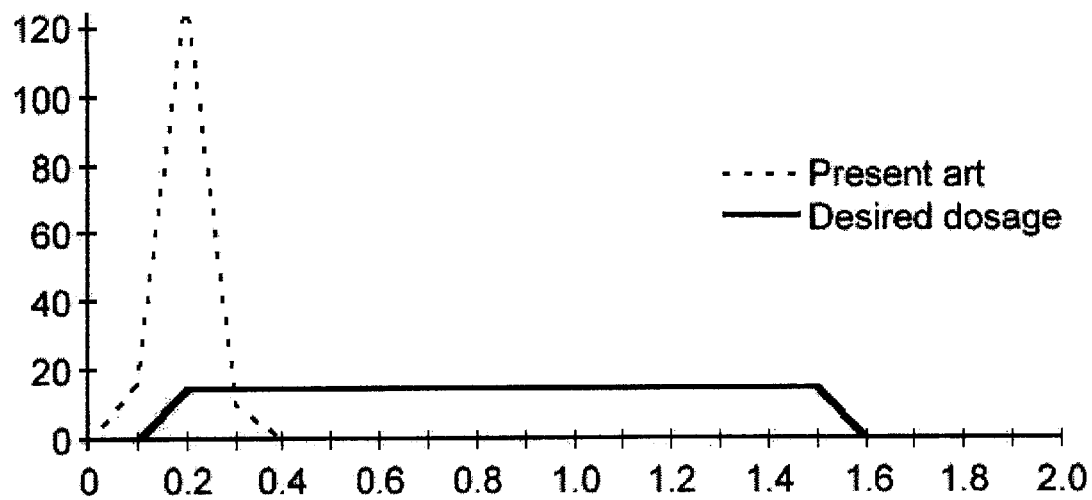
FIG. 1 is graph illustrating the difference between an administration of a medical composition in the form of a powder according to the state of the art compared to an administration according to the method of the present invention.

The present invention intends to provide a dosing of the substance to be administered which should be prolonged to a certain minimum period of time during an inspiration. In FIG. 1 is demonstrated a graph which by the hatched curve demonstrates the normal dosing period obtained in an inhaler according to the state of the art. All dosing power available will be released into the inspiration air during 0.2 to 0.3 seconds. A more reasonable time for releasing the dose would be of the order 1.5 to 2 second to obtain a better distribution of the substance in the inspiration air to ensure that the pharmaceutical substance really reaches the deep areas of the lung of a patient. The solid curve describes the distribution of substance according to the present inventive solution to the problem.

FIG. 2 illustrates a first embodiment presenting a disposable dosing member in the form of a drum 10 utilizing the solution according to the present invention to prolong the time during which an inhaled substance will be administered. On the cylindrical surface of the dosing drum 10 there are prepared in advance, a number of extended strings of prepared doses 15, 16 of very fine powder of the medical composition to be administered. The drum 10 is rotated around a central stud 12 in a direction indicated by an arrow 14 for selecting one of the prepared doses 16. A dosing element 7, in the form of a tube or nozzle is moved along the selected prepared dose 15 along a direction indicated by an arrow 30. The dosing element 7 is connected to a mouthpiece (not shown) of an inhaler and inspiration air will bring the medical composition into the inhaler in a manner well known to a person skilled in the art.

Figure 2:
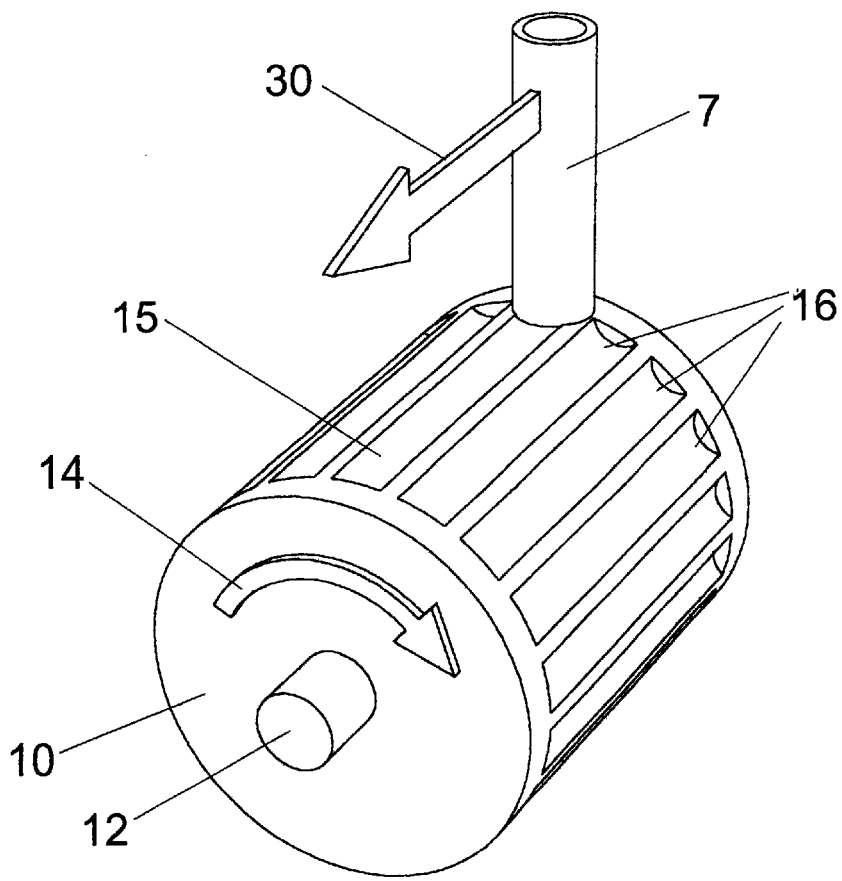
FIG. 2 illustrates a first embodiment of a dosing drum containing a number of prepared straight strings of fine powder in accordance with the present invention.

In a further embodiment the mantle of the dosing drum 10 of FIG. 2 may be provided with flat surface portions on the mantle running parallel to the central axis of the drum for the extended strings of prepared doses of powder.

Thereby it is ensured that the entire width of the string will be as close as possible to the dosing element 7 for a most efficient pick up of powder when the dosing element 7 is moving along the extended string of the medical composition during an administration operation.

Figure 3:
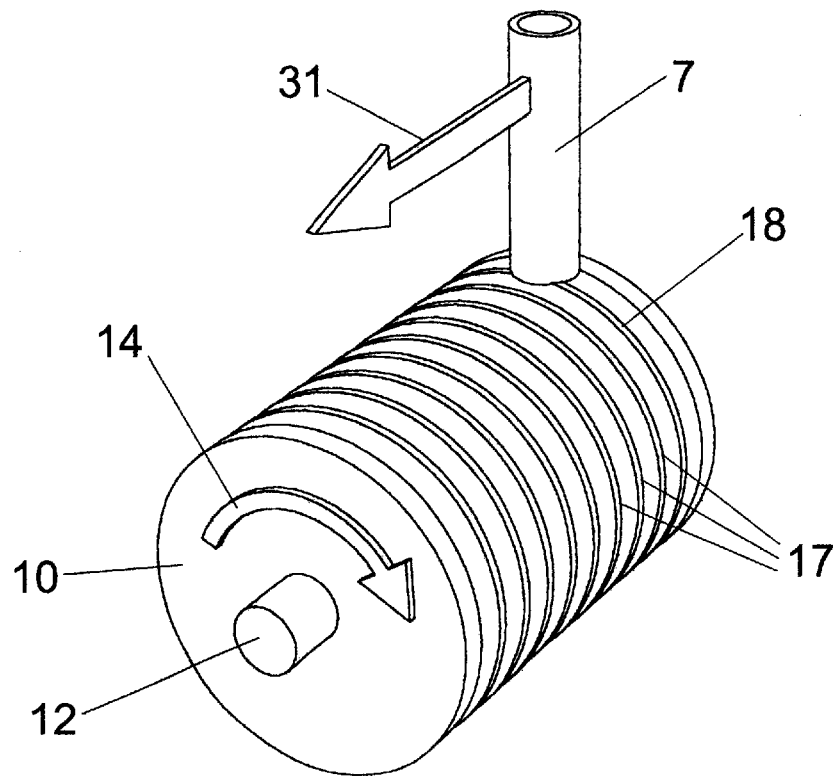
FIG. 3 illustrates a second embodiment of a dosing drum containing a number of prepared circular strings of fine powder in accordance with the present invention.

In FIG. 3 is illustrated a second embodiment of a disposable dosing drum 10 used for applying the method of the present invention. In this embodiment the strings containing a dose or even a portion of a dose are formed as concentric slots 17 encircling the dosing drum 10. A dosing element 7, in the form of a tube or nozzle is moved along a direction indicated by the arrow 31 for selecting a dose slot 18. The dosing drum is then rotated around a stud 12 in the direction of the arrow 14 during the dose administration. Similar to the first embodiment of FIG. 2 the dosing element 7 is connected to a mouthpiece (not shown) of an inhaler in a manner well known to a person skilled in the art.

Figure 4:
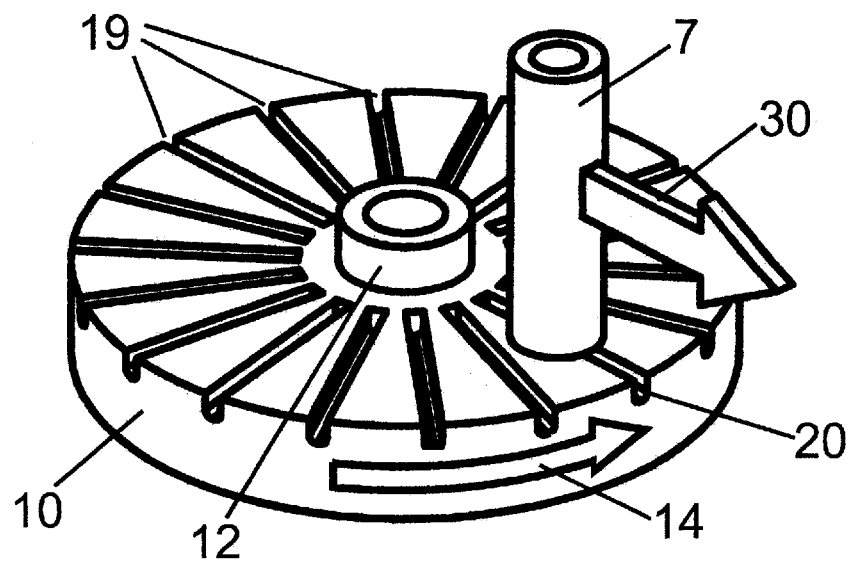
FIG. 4 illustrates a third embodiment of a dosing member in the form of a rotatable disc provided with extended dose strings of powder to be administered.

Still a further embodiment of the present invention is demonstrated in FIG. 4. The disposable member is designed as a round disc 10 having radial slots 19 for carrying the medical composition dose to be administered. By rotating the disc 10 around a central stud 12 a slot 20 will be selected by the dosing element 7, which during the inspiration is moved along that radial slot in the direction of the arrow 30 to thereby prolong the time of administration to the desired period of time of the order 1 to 2 seconds instead of a few tens of a second as in devices according to the state of the art.

Figure 5:
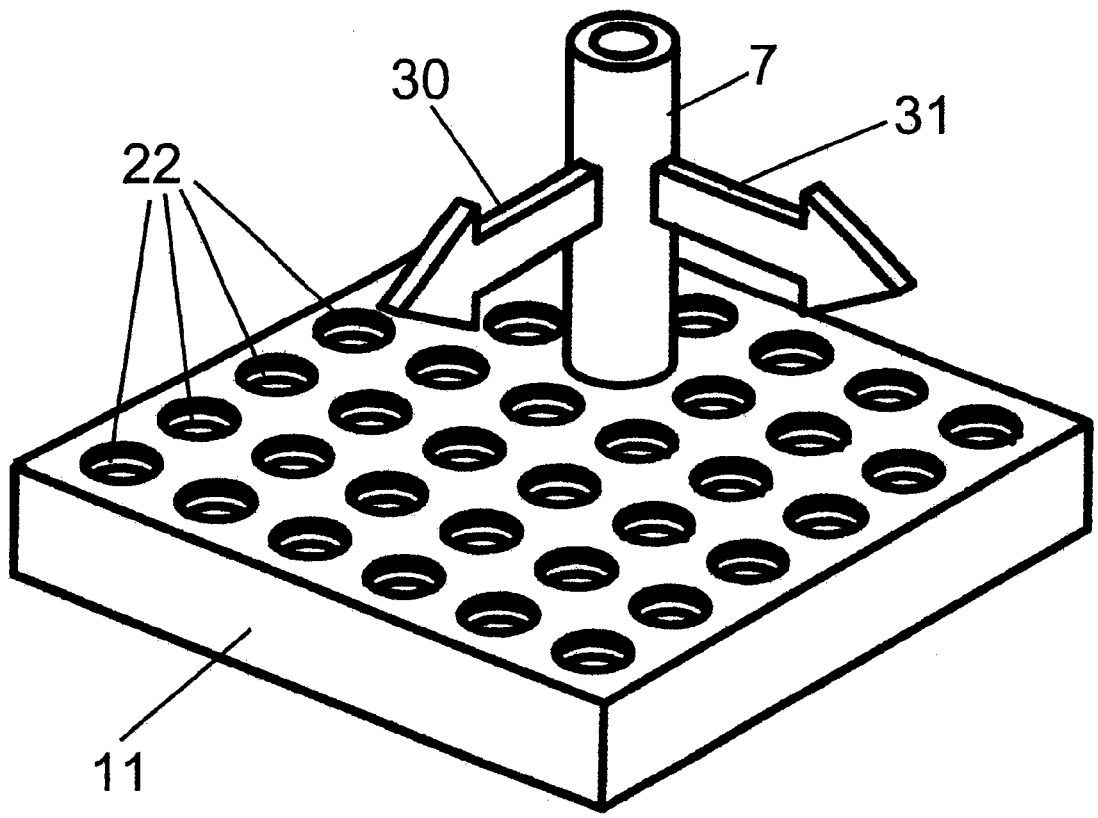
FIG. 5 illustrates a fourth embodiment of a dosing member in the form of a square plate provided with extended container rows of fine powder to be administered.

Finally FIG. 5 discloses still another embodiment of the disposable dosing member in form of a disposable square plate 11 provided with extended rows of containers for the medical composition to be administered. A row of containers 22 will for instance be selected by means of moving the dosing element 7 along a direction indicated by the arrow 31. During the inspiration the dosing element is moved in direction along the arrow 30 identical to the first embodiment. The nozzle of the dosing element 7 will then pass over a selected number of the containers 22 of the illustrative embodiment disclosed in FIG. 5. A person skilled in the art will realize that instead of the containers 22 illustrated in FIG. 5 the medical composition can be provided in extended slots running for instance in the direction of the arrow 30.

The disposable member containing a number of prefabricated doses of very small particles, preferably of the order of a few $\mu$m, will be protected in a standard way by, for instance, blister protective sheets, which preferably will be removed, one at a time, for each dose to thereby maintain the rest of the content of the disposable member in a moisture-proof condition to avoid unwanted agglomeration of the pharmaceutical substance.

In different embodiments of the inhaler device adapted for the present disposable dosing member the airspeed may be measured by means of an air flow gauge according to the state of the art for controlling and synchronizing the motion of the dosing element 7, to thereby ensure the correct release of powder during the administration. For instance, such a controlling device using an air-flow gauge is found in the inhaler described in the mentioned disclosed document WO97/00704.

It will be understood by those skilled in the art that various modifications and changes may be made to the present invention without departure from the scope thereof, which is defined by the appended claims.

What is claimed is:

1. An inhaler dosing device for administering of a pharmaceutical composition in the form of fine powder to be inhaled, comprising:

a dosing member having a surface shaped for containing plural extended doses of a powdered pharmaceutical composition; and a dosing element having an opening selectively movable adjacent to said plural extended doses, said dosing element being movable along one of the plural extended doses when administering a dose for prolonging a time period during which a pharmaceutical composition is adapted for release from the dosing member into an airstream of an inhaler arrangement during an inspiration to thereby obtain an evenly distributed amount of the composition in the inspiration air.

2. The inhaler dosing device according to claim 1, wherein said dosing member comprises a circular drum with the plural extended doses on a cylindrical surface thereof.

3. The inhaler dosing device according to claim 2, wherein said dosing member constitutes a replaceable disposable package in advance prepared with a number of extended doses containing the pharmaceutical composition to be administered.

4. The inhaler device according to claim 1, wherein said dosing member is a disc with radially extending slots for the plural extended doses.

5. The inhaler dosing device according to claim 4, wherein said dosing member constitutes a replaceable disposable package in advance prepared with a number of extended doses containing the pharmaceutical composition to be administered.

6. The inhaler dosing device according to claim 1, wherein said dosing member is a plate with a plurality of container rows for the plural extended doses.

7. The inhaler dosing device according to claim 6, wherein said dosing member constitutes a replaceable disposable package in advance prepared with a number of extended doses containing the pharmaceutical composition to be administered.

8. The inhaler dosing device according to claim 1, wherein an envelope surface of said dosing member forms a number of elongated generally flat surfaces, each flat surface carrying one of the plural extended doses.

9. The inhaler dosing device according to claim 8, wherein said dosing member constitutes a replaceable disposable package in advance prepared with a number of extended doses containing the pharmaceutical composition to be administered.

10. The inhaler dosing device according to claim 1, wherein an envelope surface of said dosing member forms a number of circularly distributed tracks for the plural extended doses.

11. The inhaler dosing device according to claim 10, wherein said dosing member constitutes a replaceable disposable package in advance prepared with a number of extended doses containing the pharmaceutical composition to be administered.

12. The inhaler dosing device according to claim 1, wherein said dosing member constitutes a replaceable disposable package in advance prepared with a number of extended doses containing the pharmaceutical composition to be administered.

13. An inhaler dosing device for administering a pharmaceutical composition in the form of a fine powder to be inhaled, comprising:
    a dosing member having a plurality of elongated slots; and
    a dosing element movable from a first position to a second position along one of said plurality of elongated slots, when said inhaler dosing device is administering a single dose of a pharmaceutical composition.

14. The inhaler dosing device according to claim 13, wherein the dosing element is a drum and the plurality of elongated slots extend longitudinally across the drum.

15. The inhaler dosing device according to claim 13, wherein the dosing member is a drum and the plurality of elongated slots are concentrically encircling the drum.

16. The inhaler dosing device according to claim 13, wherein the dosing element is a disk and the plurality of elongated slots extend radially from a central axis of the disk.

17. An inhaler dosing device for administering a pharmaceutical composition in the form of a fine powder to be inhaled, comprising:
    a dosing member having a plurality of rows, each row having a plurality of containers adapted for containing a pharmaceutical composition; and
    a dosing element movable from a first position over one of said plurality of containers in one of said rows to a second position over another one of said plurality of containers in said row, when said inhaler dosing device is administering one dose of a pharmaceutical composition.

* * * * *